United States Patent [19]

Tanaka et al.

[11] Patent Number: 5,994,565

[45] Date of Patent: Nov. 30, 1999

[54] PROCESS FOR PRODUCING PURIFIED ε-CAPROLACTONE

[75] Inventors: Kazuo Tanaka; Atsushi Okoshi; Hiroshi Ogawa, all of Kurashiki, Japan

[73] Assignee: Mitsubishi Gas Chemical Company, Inc., Japan

[21] Appl. No.: 09/271,966

[22] Filed: Mar. 18, 1999

[30] Foreign Application Priority Data

Mar. 19, 1998 [JP] Japan ................................. 10-070450
Oct. 22, 1998 [JP] Japan ................................. 10-301079

[51] Int. Cl.⁶ ................................................. C07D 313/04
[52] U.S. Cl. .............................................................. 549/272
[58] Field of Search ............................................... 549/272

[56] References Cited

U.S. PATENT DOCUMENTS

| 4,313,879 | 2/1982 | Klenk et al. ............................. 549/272 |
| 4,341,709 | 7/1982 | Hofen et al. ............................. 549/272 |
| 4,870,192 | 9/1989 | Chang et al. ............................ 549/272 |
| 4,994,583 | 2/1991 | Pralus et al. ............................ 549/272 |

FOREIGN PATENT DOCUMENTS

| 822 193 A2 | 2/1998 | European Pat. Off. . |
| 5-1054 | of 1993 | Japan . |

*Primary Examiner*—Amelia Owens
*Attorney, Agent, or Firm*—Leydig, Voit & Mayer, Ltd.

[57] ABSTRACT

A process for producing purified ε-caprolactone from an ε-caprolactone-containing reaction product produced by the oxidation of cyclohexanone comprising subjecting the ε-caprolactone-containing reaction product to an alkali-treatment in the presence of an inert gas atmosphere or to a heat treatment in the presence of an inert gas atmosphere or to a combined alkali-treatment and heat treatment, and distilling the treated reaction product.

3 Claims, No Drawings

PROCESS FOR PRODUCING PURIFIED ε-CAPROLACTONE

FIELD OF THE INVENTION

The present invention relates generally to a process for producing purified ε-caprolactone. ε-caprolactone is useful as a raw material for the preparation of ε-caprolactam and as a raw material for the preparation of polyurethane.

BACKGROUND OF THE INVENTION

ε-caprolactone is a high boiling point liquid with excellent reactivity. ε-caprolactone is used as a raw material in the preparation of polyesterpolyol, urethane resin and the like. Thus, polyesterpolyol for polyurethane and high molecular weight polyesterpolyol, which are produced from ε-caprolactone, are used as blending agents to improve the properties of various resins.

When polyesterpolyol obtained from ε-caprolactone is blended with polyethylene, gloss, transparency and blocking preventive ability are improved. When ε-caprolactone is blended with polyvinyl chloride, low temperature embrittlement of polyvinyl chloride is improved. However, the properties of ε-caprolactone, particularly its appearance, including its color and the like, often affect the properties of the blended resins, including, for example, their appearance, weather resistance, and the like.

Various treatments have been used heretofore to improve the properties of ε-caprolactone. Particularly, repetitious purifying distillation using a 10–30 stage distillation column, preservation under nitrogen atmosphere and addition of a stabilizer such as p-methoxyphenol, tridecylphosphite, 2,6-ditertiary-butyl-r-methylphenol, and the like, have been conducted on ε-caprolactone to improve its purity. Additionally, adsorbents have been used in the purification process. For example, Japanese Patent Kokai (laid-open) No. 5-1054 describes to the use of a hydrotalcite compound as the adsorbent.

To improve the color of ε-caprolactone, repetitious purifying distillation requires large distillation columns and a large amount of heat. Addition of a stabilizer is not satisfactory because it worsens the appearance of urethane resin produced from the lactone polyol. Use of a hydrotalcite compound as the adsorbent is expensive, and thus undesirable. Thus, conventional methods for the purification of ε-caprolactone are unfavorable, and the present invention offers significant improvement for obtaining purified ε-caprolactone.

SUMMARY OF THE INVENTION

An object of the present invention is to provide a method for producing high quality ε-caprolactone on an industrial scale without repeating the purifying distillation in large columns with a large amount of heat or without using costly stabilizer or adsorbent for the improvement of color. Advantageously, the high quality ε-caprolactone can be used to make polymers or polymer blends with improved polymer appearance.

The present inventors assiduously conducted investigations to solve the problems of the prior art processes, and have found that a high quality ε-caprolactone can be produced advantageously on an industrial scale by subjecting the ε-caprolactone-containing distillate of the purification column to an alkali-treatment and/or heat treatment at a temperature of 130° C. or higher in an inert gas atmosphere, and then distilling the treated distillate by simple distillation or by using a distillation column of five stages or less.

That is, the present invention provides a process for producing a purified ε-caprolactone which comprises removing impurities by distillation from a reaction product containing ε-caprolactone produced by oxidation of cyclohexanone, wherein the distillate of the purification column is treated by alkali-treatment and/or heat treatment at a temperature of 130° C. or higher in an inert gas atmosphere and then distilled either by simple distillation or by using a distillation column of five stages or less.

DETAILED DESCRIPTION OF THE INVENTION

The process for producing ε-caprolactone, in accordance with the present invention, is preferably used to purify ε-caprolactone produced by the oxidation of cyclohexanone. There are co-oxidation processes where both cyclohexanone and an aromatic aldehyde are oxidized and a process where cyclohexanone is oxidized in the presence of organic peracetic acid or hydrogen peroxide. The process of the present invention can be used to purify the ε-caprolactone produced by either of these processes, or any other process involving the oxidation of cyclohexanone.

The reaction products containing ε-caprolactone are obtained by these reactions, i.e., the oxidation of cyclohexanone, and the purified ε-caprolactone is produced by removing impurities from the reaction product.

For example, the reaction product obtained by the co-oxidation process using 2,4-dimethylbenzaldehyde as the aromatic aldehyde contains ε-caprolactone and impurities including 2,4-dimethyl benzoic acid, cyclohexanone, 2,4-dimethylbenzaldehyde and other unknown byproducts.

The reaction product is distilled sequentially, so that unreacted cyclohexanone (boiling point 155.6° C.) is initially removed and then 2,4-dimethyl benzoic acid (boiling point 267° C.) and 2,4-dimethyl-benzaldehyde (boiling point 225° C.) are removed and the ε-caprolactone (boiling point 235.3° C.) is finally obtained in a purifying distillation column. The removal of low boiling substances and high boiling substances is usually conducted by vacuum distillation since it is desirable that distillation be done at as low a temperature as is possible in order to avoid a change in the quality of the ε-caprolactone during the distillation. The purity of the distillate from the purifying distillation column is preferably more than 98% by weight.

In accordance with the present invention, the ε-caprolactone-containing reaction product obtained from the purifying distillation process described above is further purified by subjecting the distillate to either an alkali-treatment, or to a heat treatment, or to a combination of an alkali-treatment and heat treatment. In keeping with the present invention, the alkali-treatment and heat treatment are carried out in an inert gas atmosphere. Generally, the inert gas used in the present invention is nitrogen, although any of the noble gases may also be used.

The alkali compounds of alkali metals or alkaline earth metals are used for the alkali-treatment of the distillate from the purifying distillation column. The hydroxides, carbonate salts, hydrocarbon salts, oxides and/or mixtures of these compounds are suitable for use in the process of the present invention. By way of illustration and not in limitation of the present invention, sodium hydroxide, calcium hydroxide, lithium hydroxide, barium hydroxide, magnesium hydroxide, strontium hydroxide, potassium hydroxide, sodium carbonate, potassium carbonate, calcium carbonate, barium carbonate, magnesium carbonate, sodium hydrocarbonate, potassium hydrocarbonate, calcium oxide, magnesium oxide and barium oxide are suitable for use for the alkali-treatment. These compounds can be used alone or in combination.

The amount of alkali compound used in the alkali-treatment is from about 0.01 to about 1000 ppm and preferably 0.1 to 100 ppm by weight of ε-caprolactone used in the process of the present invention, when the alkali compound is soluble in ε-caprolactone.

Alkali compounds which are insoluble in ε-caprolactone are used by adding them in powder form to the distillate from the purifying distillation and suspending and stirring them in the distillate. The amount of the alkali compound used in the alkali-treatment is from about 1 to about 100,000 ppm and preferably from about 10 to about 10,000 ppm by weight of ε-caprolactone when the alkali compounds are insoluble in ε-caprolactone.

The temperature of the alkali-treatment may be room temperature or more. Preferably, the alkali-treatment temperature is from about 50° to about 200° C., and more preferably from about 70° to about 180° C. in order to increase the speed of treatment, or to decrease the viscosity of the distillate. While at higher temperature the color of the polymer is improved, the quality of the ε-caprolactone is apt to change due to polymerization or similar reactions.

The alkali-treatment time is generally in the range of from about 5 minutes to about 10 hours, and preferably from about 30 minutes to about 5 hours, depending upon the temperature.

The alkali-treatment and heat treatment may be combined in the process of the present invention as stated above. The temperature of heat treatment may be lowered by conducting it together with alkali-treatment to avoid changing the quality of the ε-caprolactone by polymerization or the like.

Insoluble substances contained in the ε-caprolactone are apt to be a cause of blocking in the reboiler of the distillation column, etc., so insoluble substances are preferably removed by a filter. After filtration to remove insolubles, the ε-caprolactone is purified by simple distillation or using a distillation column of five stages or less.

The temperature of the heat treatment when alkali-treatment is not carried out, is 130° C. or more, preferably from about 135° C. to about 210° C. The color of the polymer is improved at the higher temperatures in this range, however, the quality of ε-caprolactone is apt to suffer due to polymerization or the like or due to a decrease in the purity of the ε-caprolactone resulting from decomposition or the like.

Treatment time in the absence of the alkali-treatment is generally from about 30 minutes to about 5 hours, and preferably from about 1 hour to about 4 hours. Treatment time depends somewhat upon the temperature of the treatment.

The colored components are transformed into high boiling substances by alkali-treatment or heat treatment, and ε-caprolactone is purified by removing the high boiling substances by simple distillation or by using a distillation column of five stages or less.

The present invention may be carried out batch wise or continuously, however, the continuous process is preferable.

According to the present invention, high quality, ε-caprolactone with improved color in resulting polymers is obtained by a simple distillation after the alkali-treatment or heat treatment in inert gas atmosphere.

The present invention is thermally preferable because repeated purifying distillations are not required. The appearance of urethane resin using lactone polyol is not spoiled because no stabilizer is used. And the present invention is economically preferable because expensive adsorbent is not added.

PREFERRED EMBODIMENTS OF THE INVENTION

Some of the preferred embodiments of the present invention will be explained in more detail by referring to Examples and Comparative Examples, which are not intended to limit the scope of the present invention.

In the Examples and Comparative Examples below, "polymer color" was obtained by the following method: the polymer test was conducted by heating the mixture of ε-caprolactone 150 g, ethylene glycol 5 g and tin butyloxide 0.2 g for 2 hours at 170° C., and then melting the polymer thus obtained in a nitrogen shielded color tube. Then the color of the polymer is compared with APHA standard colors obtained according to JIS K 1557 6.2.

REFERENCE EXAMPLE

Production of ε-caprolactone

A mixture liquid containing 80% by weight (hereinafter "wt %") of cyclohexanone, 20 wt % of 2,4-dimethylbenzaldehyde and 1 ppm (as cobalt) of cobalt naphthate as catalyst was fed at the rate of 3000 g/hr to a flow pass type autoclave having interior capacity of 6L, provided with a stirrer. The continuous reaction was conducted at a reaction temperature of 35° C. under a pressure 25 kg/cm$^2$ G, while adjusting air charge to reduce the oxygen concentration in the off gas to 10 vol %. The reaction product was drawn out continuously to maintain a constant liquid level.

The amount of the reaction product drawn at a steady state was 3086 g/h. The components of the reaction mixture were ε-caprolactone 7.92 wt %, 2,4-dimethylbenzoic acid 12.75 wt %, 2,4-dimethylbenzaldehyde 7.58 wt %, cyclohexanone 70.60 wt % and other components 1.15 wt %. The hold-up time of the reaction mixture was 0.97 hour and conversion of the 2,4-dimethylbenzaldehyde was 61.0%.

From the reaction product thus obtained, cyclohexanone was separated by film evaporator, and then 2,4-dimethylbenzoic acid and other higher boiling components, the remaining cyclohexanone, unreacted 2,4-dimethylbenzaldehyde and the other lower boiling components were removed by distillation. Then the higher boiling components were removed by purifying distillation using a 20-stage distillation column. The obtained distillate of ε-caprolactone (purity; 99.5 wt %) was used for the following Examples and Comparative Examples.

EXAMPLE 1

One-half gram of sodium carbonate was added to 1000 g of ε-caprolactone obtained in the Reference Example, and held at 120° C. for 1 hour in a nitrogen atmosphere. Thereafter, the insoluble sodium carbonate was removed by filtration. The filtrate was distilled batch-wise using a theoretical 3 stage distillation column to obtain purified ε-caprolactone at 90% yield to ε-caprolactone feed.

The polymer test of the ε-caprolactone was conducted, and the polymer color as APHA 30.

COMPARATIVE EXAMPLE 1

Without adding sodium carbonate, ε-caprolactone was treated as in Example 1. The polymer color was APHA 55.

EXAMPLES 2 through 6

Changing the type of alkali compounds and the amount thereof, Examples 2 through 6 were carried out. Other conditions were the same as in Example 1. The type of alkali compound, the amount thereof and the results for polymer made using ε-caprolactone made by the process of the present invention in Examples 1–6 are shown in Table 1.

TABLE 1

|  | Alkali compounds | Amount | Polymer |
| --- | --- | --- | --- |
| Ex. 1 | Sodium carbonate | 500 ppm | APHA 30 |
| Ex. 2 | Sodium hydrogen carbonate | 500 | 30 |
| Ex. 3 | Sodium hydroxide | 10 | 35 |
| Ex. 4 | Potassium hydroxide | 10 | 35 |
| Ex. 5 | Magnesium oxide | 2500 | 40 |
| Ex. 6 | Barium oxide | 2500 | 40 |
| Comp. Ex. 1 | — | — | 55 |

From the results of Table 1, the improvements in the polymer color due to distillation after alkali-treatment of ε-caprolactone were confirmed.

EXAMPLE 7

The ε-caprolactone (1000 g) obtained in the Reference Example was heated to 140° C. for 3 hours in a nitrogen atmosphere, and distilled continuously by simple distillation to obtain purified ε-caprolactone of 99.9% purity at 98% yield to the ε-caprolactone feed.

The polymer test of the ε-caprolactone was conducted, and the polymer color was APHA 30.

COMPARATIVE EXAMPLE 2

The same treatment as in Example 7 was carried out except that heating temperature was conducted at 120° C. The polymer color was APHA 55.

COMPARATIVE EXAMPLE 3

The polymer test of the ε-caprolactone was conducted using ε-caprolactone obtained in the Reference Example without heat treatment. Then the polymer color was APHA 60.

Example 7 and Comparative Examples 2 and 3 demonstrate that the polymer made from ε-caprolactone purified by heat treatment in an inert gas atmosphere in accordance with the present invention has improved color.

EXAMPLE 8

The same treatment as Example 7 was carried out except that the heating temperature was 150° C., to obtain purified ε-caprolactone of 99.9%. The polymer color was APHA 25.

EXAMPLE 9

The same treatment of Example 7 was carried out except heating temperature was conducted at 200° C. to obtain purified ε-caprolactone of 99.9% purity. The polymer color was APHA 15.

EXAMPLE 10

One-half gram of sodium carbonate was added to 1000 g of ε-caprolactone obtained in the Reference Example, and held at 140° C. for 3 hours in a nitrogen atmosphere. Thereafter, insoluble sodium carbonate was filtered off. The filtrate was distilled continuously using a simple distillation column to obtain purified ε-caprolactone of 99.9% at 98% yield to ε-caprolactone feed.

The polymer test of the ε-caprolactone was conducted, and the polymer color as APHA 20.

This Example illustrates that the color of polymer prepared with ε-caprolactone, purified using a combined alkali-treatment and heat treatment in accordance with the present invention, is improved.

What is claimed is:

1. A process for producing purified ε-caprolactone which comprises:

forming a first distillate by distilling an ε-caprolactone-containing reaction product produced by the oxidation of cyclohexanone;

forming a treated distillate by subjecting the first distillate to a treatment step selected from the group consisting of an alkali-treatment in the presence of an inert gas atmosphere, a heat treatment at a temperature of at least 130° C. in an inert gas atmosphere or a combination of an alkali-treatment and a heat treatment in an inert atmosphere at atmosphere of at least 130° C., and;

distilling the treated distillate in a distillation step selected from the group consisting of simple distillation or distillation in a column of less than five stages.

2. A process for producing a purified ε-caprolactone according to claim 1, wherein the alkali-treatment uses alkali metal compounds and/or alkali earth metal compounds.

3. A process for producing a purified ε-caprolactone according to claim 1, wherein heat treatment is conducted at a temperature of from about 135° C. to about 210° C.

* * * * *